United States Patent [19]

Fischer et al.

[11] Patent Number: 5,414,097
[45] Date of Patent: May 9, 1995

[54] PURIFICATION OF ESTERS OF TETRAHYDRO-PYRAN-4-CARBOXYLIC ACID

[75] Inventors: Rolf Fischer, Heidelberg; Norbert Goetz, Worms; Thomas Kuekenhoehner, Boehl-Iggelheim; Harald Rust, Neustadt; Werner Schnurr, Herxheim, all of Germany

[73] Assignee: BASF Aktiengesellschaft, Ludwigshafen, Germany

[21] Appl. No.: 185,179

[22] Filed: Jan. 24, 1994

Related U.S. Application Data

[63] Continuation-in-part of Ser. No. 990,285, Dec. 14, 1992, abandoned.

[30] Foreign Application Priority Data

Dec. 13, 1991 [DE] Germany .................. 41 41 221.4

[51] Int. Cl.⁶ ............................................. C07D 309/08
[52] U.S. Cl. ................................................... 549/425
[58] Field of Search ...................................... 549/425

[56] References Cited

U.S. PATENT DOCUMENTS 4,837,346  6/1989  Fischer et al. .................. 549/425

*Primary Examiner*—Nicky Chan
*Attorney, Agent, or Firm*—Keil & Weinkauf

[57] ABSTRACT

A process for purifying esters of tetrahydropyran-4-carboxylic acid of the formula I

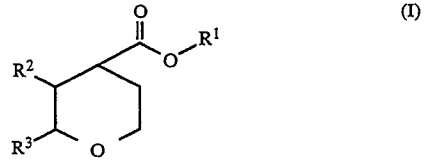

where
$R^1$ to $R^3$ are each $C_1$–$C_4$-alkyl, and $R^2$ and $R^3$ are each additionally hydrogen, from mixtures produced in the reaction of butyrolactones of the formula II

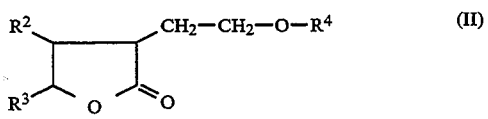

where
$R^2$ and $R^3$ have the abovementioned meanings, and $R^4$ is hydrogen, alkyl of 1–6 carbons or acyl of the formula —CO—$R^2$, with alcohols of the formula $R^1OH$ in the presence of oxide catalysts, by distillation, which entails
a) removing overhead, in a first column with 5–25 theoretical plates with a distillate pressure of 700–1100 mbar and a distillate temperature of 50°–80° C., an alcohol and up to 10% of the water,
b) transferring the bottom product from the first column into a second column with 18–40 theoretical plates, into which a water entrainer is metered between plates 15 and 30, and is circulated, and which operates with a distillate pressure of 35–350 mbar and a distillate temperature of 18°–70° C., with the esters of tetrahydropyran-4-carboxylic acid being removed between plates 8 and 18 at 90°–150° C., and, where appropriate,
c) feeding the bottom product from the second column into a third column with 5–25 theoretical plates, and returning the overhead products at a distillate pressure of 1–100 mbar and a distillate temperature of 90°–140° C. to the synthesis of the esters of tetrahydropyran-4-carboxylic acid.

2 Claims, 1 Drawing Sheet

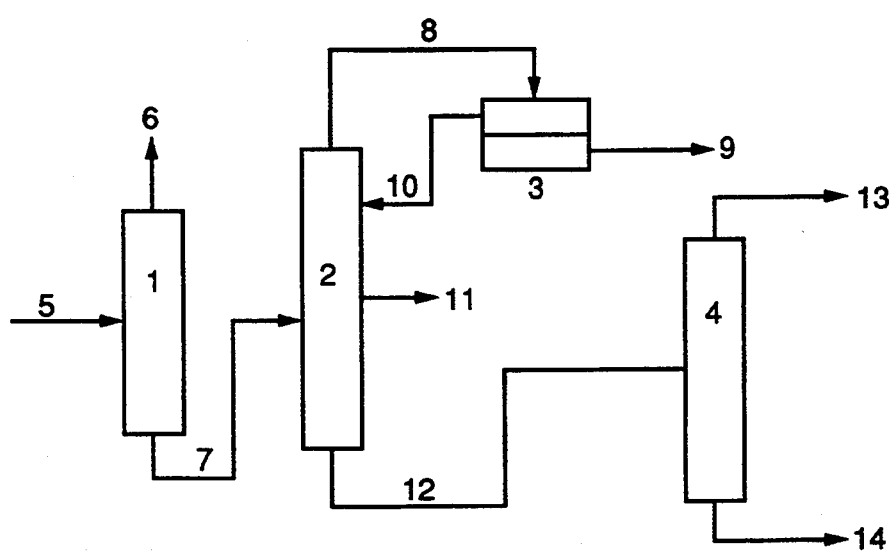

PURIFICATION OF ESTERS OF TETRAHYDRO-PYRAN-4-CARBOXYLIC ACID

This application is a c-i-p of application Ser. No. 07/990,285, filed on Dec. 14, 1992 now abandoned.

The present invention relates to a process for purifying esters of tetrahydropyran-4-carboxylic acid as are produced in the reaction of 3-(2-hydroxyethyl)- and 3-(2-acyloxyethyl)butyrolactones with lower alcohols in the presence of oxide catalysts.

Esters of tetrahydropyran-4-carboxylic acid are important intermediates for preparing 4-formyltetrahydropyran.

It is known that 3-(2-hydroxyethyl)butyrolactone can be reacted with methanol to give esters of tetrahydropyran-4-carboxylic acid (EP-A-284 969). This reaction results in a mixture containing esters of tetrahydropyran-4-carboxylic acid, 3-(2-hydroxyethyl)butyrolactone, 3-(2-methoxyethyl)butyrolactone, 3-spirocyclopropylbutyrolactone, methanol, possibly water, possibly acetic acid and possibly methyl acetate, which involves problems in working up.

It is an object of the present invention to develop a process for purifying esters of tetrahydropyran-4-carboxylic acid from mixtures of this type.

We have found that this object is achieved by a novel and improved process for purifying esters of tetrahydropyran-4-carboxylic acid of the formula I

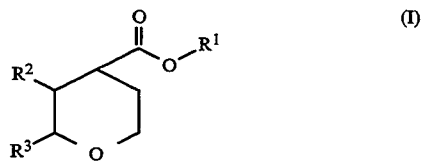

where
R$^1$ to R$^3$ are each C$_1$-C$_4$-alkyl, and R$^2$ and R$^3$ are each additionally hydrogen, from mixtures produced in the reaction of butyrolactones of the formula II

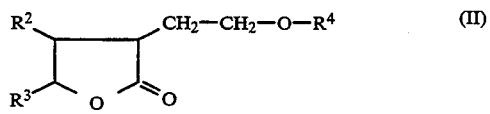

where R$^2$ and R$^3$ have the abovementioned meanings, and R$^4$ is hydrogen, alkyl of 1-6 carbons or acyl of the formula —CO—R$^2$, with alcohols of the formula R$^1$OH in the presence of oxide catalysts, by distillation, which comprises a) removing overhead, in a first column with 5-25 theoretical plates with a distillate pressure of 700-1100 mbar and a distillate temperature of 50°-80° C., an alcohol and up to 10% of the water, b) transferring the bottom product from the first column into a second column with 18-40 theoretical plates, into which a water entrainer is metered between plates 15 and 30, and is circulated, and which operates with a distillate pressure of 35-350 mbar and a distillate temperature of 18°-70° C., with the esters of tetrahydropyran-4-carboxylic acid being removed between plates 8 and 18 at 90°-150° C., and, where appropriate, c) feeding the bottom product from the second column into a third column with 5-25 theoretical plates, and returning the overhead products at a distillate pressure of 1-100 mbar and a distillate temperature of 90°-140° C. to the synthesis of the esters of tetrahydropyran-4-carboxylic acid.

The mixtures containing crude esters of tetrahydropyran-4-carboxylic acid I used for the novel process are obtained, for example, from the rearrangement of 3-(2-hydroxyethyl)butyrolactone II with methanol. They have the following composition, for example: 15-30% by weight of esters of tetrahydropyran-4-carboxylic acid, 15-25% by weight of methanol, 5-25% by weight of water, 5-20% by weight of 3-(2-methoxyethyl)butyrolactone, 5-15% by weight of 3-spirocyclopropylbutyrolactone, 0.05-15% by weight of 3-(2-hydroxyethyl)butyrolactone and 0.1-3% by weight of high boilers.

The novel process is carried out using three columns as follows, for example: In a first column which has 5-25 theoretical plates, 95-100% of the alcohol R$^1$-OH and up to 10% of the water are distilled out of the mixture overhead. The mixture can be returned to the synthesis of the esters of tetrahydropyran-4-carboxylic acid. The distillate temperatures and pressures are 50°-80° C. and 700-1100 mbar. The reflux ratio is from 1 to 10.

The bottom product from the first column, which contains the ester of tetrahydropyran-4-carboxylic acid, 3-(2-methoxyethyl)butyrolactone, 3-spirocyclopropylbutyrolactone, 3-(2-hydroxyethyl)butyrolactone, water and possibly remaining alcohol R$^1$—OH, plus high boilers, is fed into the second column with 18-40 theoretical plates. In addition, a water entrainer, eg. xylene, is metered in between plates 15 and 30. An overhead product which is composed of water and the water entrainer is obtained with a distillate pressure of 35-350 mbar and a distillate temperature of 18°-70° C. The water entrainer is returned to the column, and the water is returned to the synthesis of the esters of tetrahydropyran-4-carboxylic acid, via a phase separator. The reflux ratio is from 1 to 9. The ester of tetrahydropyran-4-carboxylic acid is removed at 90°-150° C. from between plates 8 and 18.

The bottom product from the second column, which may contain 3-(2-methoxyethyl)butyrolactone, 3-spirocyclopropylbutyrolactone and 3-(2-hydroxyethyl)butyrolactone plus high boilers, is fed into a third column with 5-25 theoretical plates in which 3-(2-methoxyethyl)butyrolactone, 3-spirocyclopropylbutyrolactone and 3-(2-hydroxyethyl)butyrolactone are removed overhead and can be returned to the synthesis of the esters of tetrahydropyran-4-carboxylic acid. The distillate temperatures and pressures in the third column are 90-140° C and 1-100 mbar. The reflux ratio is, for example, from 1 to 10.

A water entrainer is used to remove the water in the second column. Examples of water entrainers which can be used are cyclohexane, cyclohexene, benzene, toluene, hexane, heptane, CCl$_4$, chloroform, acetonitrile, pyridine or piperidine, especially xylenes or the mixture of xylene isomers.

If the rearrangement to esters of tetrahydropyran-4-carboxylic acid is carried out with esters like 3-(2-acetoxyethyl)butyrolactone in place of 3-(2-hydroxyethyl)butyrolactone, for example, the composition of the discharge changes as follows: 15-30% by weight of ester of tetrahydropyran-4-carboxylic acid, 15-30% by weight of methanol, 5-15% by weight of methyl acetate, 5-25 % by weight of water, 2-10% by weight of acetic acid, 5-20% by weight of 3-(2-methoxyethyl)-butyrolactone, 2-15% by weight of 3-spirocyclopropyl-butyrolactone, 0.05-10% by weight of 3-(2-hydroxyethyl)butyrolactone/3-(2-acetoxyethyl)butyrolactone and 0.1-3% by weight of high boilers.

Workup is carried out as in the described process with the difference that methyl acetate is removed in addition to methanol overhead in the first column. The small amounts of acetic acid which may be present in the mixture are removed with the water in the second column.

If the by-products are not to be returned to the synthesis stage, it is possible to separate 3-(2-methoxyethyl)butyrolactone and 3-spirocyclopropylbutyrolactone in another distillation column.

$R^1$, $R^2$ and $R^3$ are each, independently of one another, $C_1$-$C_4$-alkyl such as methyl, ethyl, n-propyl, isopropyl, n-butyl, isobutyl, sec-butyl and tert-butyl, preferably methyl and ethyl, particularly preferably methyl, and $R^2$ and $R^3$ are additionally particularly preferably each hydrogen.

$R^4$ is $C_1$-$C_6$-alkyl such as methyl, ethyl, n-propyl, isopropyl, n-butyl, isobutyl, sec-butyl and tert-butyl, preferably methyl and ethyl, particularly preferably methyl, as well as hydrogen and —CO—$R^2$.

Esters of tetrahydropyran-4-carboxylic acid can be separated from the starting mixtures particularly advantageously by this process. The azeotropic removal of water means that one distillation step can be omitted because the esters of tetrahydropyran-4-carboxylic acid can be discharged at the side of the same column. It is also possible in principle to obtain higher esters ($C_1$-$C_4$) by this process.

The sole FIGURE in the drawing is a schematic diagram of the process of this invention.

EXAMPLE

A reaction mixture which was obtained by a catalytic rearrangement of 3-(2-acetoxyethyl)butyrolactone and which had the following composition was distilled:
23.8% by weight of ester of tetrahydropyran-4-carboxylic acid,
3.3% by weight of 3-spirocyclopropylbutyrolactone,
7.9% by weight of 3-(2-methoxyethyl)butyrolactone,
2.4% by weight of 3-(2-hydroxyethyl)butyrolactone,
5.2% by weight of 3-(2-acetoxyethyl)butyrolactone,
2.5% by weight of acetic acid,
8.5% by weight of methyl acetate,
26.3% by weight of methanol and
15.9% by weight of water.

A diagram of the distillation apparatus is shown in the drawing. 1000 parts of the mixture are passed through feed line (5) into the first column (1). The column has 10 theoretical plates. With a distillate temperature of 63° C. and a distillate pressure of 900 mbar, and with a reflux ratio of 3:1, 320 parts of an overhead product (6) with the composition 74% by weight of methanol, 20.7% by weight of methyl acetate and 3.2% by weight of water are obtained. The bottom product comprises 680 parts of a mixture of 33.6% by weight of ester of tetrahydropyran-4-carboxylic acid, 4.8% by weight of 3-spirocyclopropylbutyrolactone, 11.9% by weight of 3-(2-methoxyethyl)butyrolactone, 3.9% by weight of 3-(2-hydroxyethyl)butyrolactone, 6.3% by weight of 3-(2-acetoxyethyl)butyrolactone, 3% by weight of acetic acid, 0.1% by weight of methanol and 17.5% by weight of water.

100 parts of bottom product (7) from the first column (1) are passed into the second column (2) with 40 theoretical plates. 0.1 l of xylene (isomer mixture) is added as water entrainer and is returned (10) via line 8 and a phase separator (3) continuously into the column. With a distillate temperature of 28° C., a distillate pressure of 70 mbar and a reflux ratio of 1.6, 23 parts of overhead product (9) of the composition 80.1% by weight of water, 11.2% by weight of acetic acid, 3.3% by weight of methanol, 1.8% by weight of ester of tetrahydropyran-4-carboxylic acid and 44 parts of bottom product (12) with the composition 0.1% by weight of ester of tetrahydropyran-4-carboxylic acid, 10.7% by weight of 3-spirocyclopropylbutyrolactone, 28.9% by weight of 3-(2-methoxyethyl)butyrolactone, 6.1% by weight of 3-(2-hydroxyethyl)butyrolactone and 15.1% by weight of 3-(2-acetoxyethyl)butyrolactone are obtained. At 108° C., 33 parts of side stream (11) with the composition 99.5% by weight of ester of tetrahydropyran-4-carboxylic acid are removed at plate 27.

100 parts of bottom product (12) from column 2 are passed into the third column (4). At a condensate temperature of 128° C. and a distillate pressure of 3 mbar, 61 parts of overhead product (13) and 29 parts of bottom product (14) in the form of unidentified high boilers are obtained.

We claim:

1. A process for purifying esters of tetrahydropyran-4-carboxylic acid of the formula I

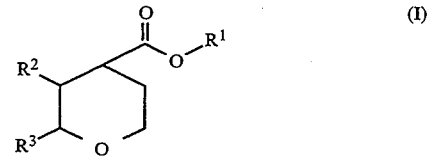

where
$R^1$ to $R^3$ are each $C_1$-$C_4$-alkyl, and $R^2$ and $R^3$ are each additionally hydrogen, from mixtures produced in the reaction of butyrolactones of the formula II

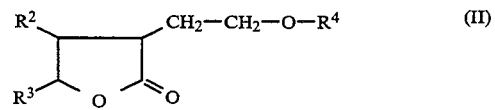

where
$R^2$ and $R^1$ have the above-mentioned meanings, and $R^4$ is hydrogen, alkyl of 1-6 carbons or acyl of the formula —CO—$R^2$, with alcohols of the formula $R^1OH$ in the presence of oxide catalysts, by distillation, which comprises
a) removing overhead, in a first column with 5-25 theoretical plates with a distillate pressure of 700-1100 mbar and a distillate temperature of 50°-80° C., an alcohol and up to 10% of the water, and
b) transferring the bottom product from the first column into a second column with 18-40 theoretical plates, into which a water entrainer is metered between plates 15 and 30, and is circulated, and which operates with a distillate pressure of 35-350 mbar and a distillate temperature of 18°-70° C., with the esters of tetrahydropyran-4-carboxylic acid being removed between plates 8 and 18 at 90°–150° C.

2. A process for purifying esters of tetrahydropyran-4-carboxylic acid of the formula I as defined in claim 1, wherein the bottom product from the second column is fed into a third column with 5–25 theoretical plates, and the overhead products from the third column are returned at a distillate pressure of 1–100 mbar and a distillate temperature of 90°–140° C. to the synthesis of the esters of tetrahydropyran-4-carboxylic acid.

* * * * *

UNITED STATES PATENT AND TRADEMARK OFFICE
CERTIFICATE OF CORRECTION

PATENT NO.: 5,414,097

DATED: May 9, 1995

INVENTOR(S): FISCHER et al.

It is certified that error appears in the above-identified patent and that said Letters Patent is hereby corrected as shown below:

Column 4, claim 1, line 52, delete "$R^1$" and substitute --$R^3$--.

Signed and Sealed this

Fifteenth Day of August, 1995

Attest:

BRUCE LEHMAN

*Attesting Officer*  *Commissioner of Patents and Trademarks*